United States Patent

Gressani et al.

[11] Patent Number: 5,208,038
[45] Date of Patent: May 4, 1993

[54] COACERVATED HIGHLY ABSORPTIVE POLYMERS

[75] Inventors: Tina M. Gressani; William L. Klein, both of New York, N.Y.

[73] Assignee: Dow Corning Corporation, Midland, Mich.

[21] Appl. No.: 448,024

[22] Filed: Dec. 8, 1989

[51] Int. Cl.$^5$ .......................... A61K 9/16; A61K 9/18
[52] U.S. Cl. ................................ 424/489; 424/501; 424/502
[58] Field of Search .............. 424/78, 81, 489, 501, 424/502, 486, 487; 523/465, 521, 223, 335; 528/497; 524/487, 277

[56] References Cited

U.S. PATENT DOCUMENTS

| | | | |
|---|---|---|---|
| Re. 27,026 | 1/1971 | Alfrey et al. | 260/2.5 |
| 2,809,943 | 10/1957 | Pye et al. | 260/2.1 |
| 3,418,262 | 12/1968 | Werotte et al. | 260/2.2 |
| 3,509,078 | 4/1970 | Roubinek et al. | 260/2.5 |
| 3,627,708 | 12/1971 | Morse et al. | 260/2.5 |
| 3,637,535 | 1/1972 | Corte et al. | 260/2.1 |
| 3,767,600 | 10/1973 | Albright | 260/2.2 |
| 3,989,649 | 11/1976 | Kailto et al. | 260/2.1 |
| 4,105,426 | 8/1978 | Iler et al. | 523/210 |
| 4,208,309 | 6/1980 | Kraemer et al. | 260/8 |
| 4,224,415 | 9/1980 | Meitzner et al. | 521/38 |
| 4,239,646 | 12/1980 | Vincent et al. | 523/335 |
| 4,661,327 | 4/1987 | Horton | 423/7 |
| 4,680,321 | 7/1987 | Graham | 523/335 |
| 4,690,825 | 9/1987 | Won | 424/501 |
| 4,719,040 | 1/1988 | Traas | 512/4 |
| 4,724,240 | 2/1988 | Abrutyn | 514/847 |
| 4,764,362 | 8/1988 | Barchas | 424/61 |
| 4,776,358 | 10/1988 | Korsk | 132/321 |
| 4,806,360 | 2/1989 | Leong | 424/487 |
| 4,813,976 | 3/1989 | Barchas | 51/293 |
| 4,828,542 | 5/1989 | Hermann | 604/3 |
| 4,874,841 | 10/1989 | Sugimori et al. | 523/335 |

FOREIGN PATENT DOCUMENTS

| | | |
|---|---|---|
| 1168157 | 5/1984 | Canada . |
| 61701 | 10/1982 | European Pat. Off. . |
| 0252463 | 1/1988 | European Pat. Off. . |
| 0306236 | 3/1989 | European Pat. Off. . |
| 2608533 | 9/1976 | Fed. Rep. of Germany . |
| 8801164 | 2/1988 | PCT Int'l Appl. . |
| 8702389 | 9/1987 | South Africa . |

OTHER PUBLICATIONS

Colloid Science Krugt vol. II 1949 pp. 247-258.

*Primary Examiner*—Thurman K. Page
*Assistant Examiner*—P. Kulkosky
*Attorney, Agent, or Firm*—Jim L. DeCesare

[57] ABSTRACT

A composition which is includes discrete particles of a highly cross-linked macroporous hydrophobic polymer. The particles are of a first predetermined average diameter, and the polymer particles have entrapped therein and dispersed uniformly throughout an active ingredient. The composition also includes a coacervating agent mixed with the polymer particles in an amount sufficient to cause the polymer particles to collect forming dense clusters of coacervated particles of a second predetermined average diameter, the second predetermined average diameter being substantially in excess of the first predetermined average diameter.

13 Claims, 6 Drawing Sheets

1000 X
0 RPM
⊢—⊣ 10 μm

FIG. 7

1000 X
75 RPM
⊢—⊣ 10 μm

COACERVATED HIGHLY ABSORPTIVE POLYMERS

BACKGROUND OF THE INVENTION

This invention relates to a macroporous highly crosslinked polymer which is coacervated into large macro particles. More particularly, the invention includes the concept of forming large particles from small porous polymer particles which entrap an active ingredient.

The concept of producing spheres or beads by means of suspension polymerization techniques is well known in the prior art. An exemplary one of such processes is disclosed in U.S. Pat. No. 2,809,943, issued Oct. 15, 1957. However, it was found that when a material was added which is a solvent for the monomers, but acts as a precipitant for the resulting polymer, a novel form of bead was provided containing a network of microscopic channels. This discovery is set forth in U.S. Pat. No. 4,224,415, filed Jul. 18, 1958, issuing some twenty-two years later on Sep. 23, 1980. In this patent, beads are produced ranging in size from about 350 to about 1200 microns. Typical monomers include divinyl toluene, diallyl maleate, and triallyl phosphate. The precipitant employed is an alkane, acid ester, or alcohol.

This technology was expanded and the precipitant was variously described in the patent literature as a diluent, porogen, active ingredient, solvent, functional material, and volatile agent. For example, in U.S. Pat. No. Re. 27,026, issued Jan. 12, 1971, porous beads of a diameter less than ten microns are disclosed. Among the monomers used to produce the beads are ethyl methacrylate, divinyl benzene, and ethylene glycol dimethacrylate. In U.S. Pat. No. 3,418,262, issued Dec. 24, 1968, there is described a bead characterized as having a rigid sponge structure, and wherein the porogenic agent employed is an acid such as stearic acid. Intermediates in bead form were produced in U.S. Pat. No. 3,509,078, issued Apr. 28, 1970, using polymeric materials such as polyethylene glycols as the precipitant material during the in situ suspension polymerization process. The macroporous character of such bead construction is graphically portrayed and illustrated in FIG. 1 of U.S. Pat. No. 3,627,708, issued Dec. 14, 1971. Beads termed "pearls" are produced, and containing active ingredients therein such as water or various alcohol ethers. The pearls are crosslinked to the extent of about twenty percent. In U.S. Pat. No. 3,637,535, issued Jan. 25, 1972, beads with a sponge structure are said to be capable of being compressed to an imperceptible powder. These beads are capable of being loaded with as much as 200-300% of active ingredients. A rigid porous bead of a trifunctional methacrylate is taught in U.S. Pat. No. 3,767,600, issued Oct. 23, 1973. Such beads have a size of 10-900 microns, and various other monomers which can be employed include diacetone acrylamide, and ethylhexyl, hydroxyethyl, and hydroxypropyl methacrylates. Paraffin wax is used to form the microscopic network of channels in U.S. Pat. No. 3,989,649, issued Nov. 2, 1976. The wax is removed from the bead structure by solvent extraction.

While many of the foregoing U.S. patents relate to ion exchange technology, a bead similar to those previously described is employed as a carrier for enzymes in U.S. Pat. No. 4,208,309, issued Jun. 17, 1980. Such beads are of the size of about 0.1 mm. U.S. Pat. No. 4,661,327, issued Apr. 28, 1987, describes a macroreticular bead containing a magnetic core. The use of hard crosslinked porous polymeric beads in cosmetics as carriers is taught in U.S. Pat. No. 4,724,240, issued Feb. 9, 1988, wherein various emollients and moisturizers are entrapped therein. These beads are said to be capable of entrapping materials such as 2-ethylhexyl oxystearate, arachidyl propionate, petroleum jelly, mineral oil, lanolin, and various siloxanes. The size of the beads ranges from 1-3,000 microns. Typical monomers include ethylene glycol dimethacrylate, lauryl methacrylate, trimethylol propane trimethacrylate, and dipentaerythritol dimethacrylate. "In situ" hydrophobic powders and "in situ" beads may be produced in accordance with the teaching of this patent. Beads having a rigid sponge structure are also described in U.S. Pat. No. 4,690,825, issued Sep. 1, 1987, and wherein the beads function as a delivery vehicle for a host of materials including pigments, vitamins, fragrances, drugs, repellants, detergents, and sun screens. The beads have a size of 10-100 microns and are preferably of a monomer system of styrene-divinyl benzene. Crosslinking is said to range from 10-40 percent. U.S. Pat. No. 4,806,360, issued Feb. 21, 1989, describes a post adsorbent bead which contains a melanin pigment for use as a sunscreen.

The foreign patent literature includes West German Offenlegungsschrift No. P-2608533.6, published Sep. 30, 1976, and wherein porous polymeric beads produced by "in situ" suspension polymerization are provided, and which are adapted to release perfumes. A controlled release of the fragrance is disclosed, providing utility for such beads in the home, automobiles, airplanes, railway cars, hospitals, classrooms, conference centers, and gymnasiums. Canadian Patent No. 1,168,157, issued May 29, 1984, describes hard, discrete, free flowing, bead constructions in which the beads entrap a series of functional materials which can be incorporated into toilet soap, body powder, and antiperspirant sticks. In European International Publication No. 0252463A2, published Jan. 13, 1988, there is disclosed a bead having a hydrophobic polymer lattice, and which entraps numerous non-cosmetic materials such as pesticides, pharmaceuticals, pheromones, and various categories of chemicals. Steroids are entrapped, for example, in the porous beads of PCT International Publication No. WO-88/01164, published on Feb. 25, 1988. The steroids are adrenocortical steroids or various anti-inflammatory type steroids. It should therefore be apparent that what began as a simple ion exchange bead concept has rapidly grown into a technology of widely varied application.

In accordance with the present invention, polymer powders are employed in novel processes not believed to be taught in the prior art, as exemplified by the foregoing patents. Those patents, in general, relate to suspension polymerization processes for the production of porous polymeric and copolymeric spheres and beads in which the precipitant is present during polymerization. These are defined as an "in situ" process.

Thus, according to the prior art, crosslinked porous copolymers in particle form can be produced by at least three distinct processes. One process produces beads by "in situ" suspension polymerization. Another process produces beads by suspension polymerization but the beads are "post adsorbed" with an active ingredient after the volatile porogen is removed. In a third process, powders are produced by "in situ" precipitation polymerization.

What has been accomplished in accordance with the present invention, however, is a unique concept differing from all of the foregoing methods, and wherein post adsorbent powders and beads are produced and used in a novel fashion.

SUMMARY OF THE INVENTION

This invention relates to a composition which is includes discrete particles of a highly cross-linked macroporous hydrophobic or hydrophilic polymer. The particles are of a first predetermined average diameter, and the polymer particles have entrapped therein and dispersed uniformly throughout, an active ingredient. The composition also includes a coacervating agent mixed with the polymer particles in an amount sufficient to cause the polymer particles to collect forming dense clusters of coacervated particles of a second predetermined average diameter, the second predetermined average diameter being substantially in excess of the first predetermined average diameter.

More particularly, the polymer can be formed of at least one polyunsaturated monomer, and the polyunsaturated monomer is one of ethylene glycol dimethacrylate and tetraethylene glycol dimethacrylate. The polymer can also be formed of and include along with a polyunsaturated monomer at least one monounsaturated monomer, and in this alternative embodiment, the monounsaturated monomer is one of lauryl methacrylate and 2-ethylhexyl methacrylate.

The particles of the first predetermined average diameter can be in the form of a bead, and the bead has an average diameter of about ten microns to about one hundred-fifty microns. Alternatively, the particles of the first predetermined average diameter can be in the form of a powder and the powder is a combined system of particles, the system of powder particles including unit particles of less than about one micron in average diameter, agglomerates of fused unit particles of sizes in the range of about twenty to eighty microns in average diameter, and aggregates of clusters of fused agglomerates of sizes in the range of about two-hundred to about twelve-hundred microns in average diameter.

The coacervating agent may be a wax such as insect and animal waxes, vegetable waxes, mineral waxes, petroleum waxes, synthetic waxes, silicone waxes, or mixtures thereof. In the case of a mixture of waxes, the preferred mixture includes mineral wax and a silicone wax, and the mineral wax is ceresin wax while the silicone wax is stearoxy dimethicone. The composition may include a dye such as D&C Violet No. 2, or Green No. 6. The polymer particles constitute from about ten to about fifty percent by weight of the composition, the active ingredient from about five to about eighty percent by weight of the composition, and the coacervating agent from about ten to about seventy percent by weight of the composition. The second predetermined average diameter of the coacervated particles is preferably in the range of from about two tenths of one millimeter to above five millimeters. The composition is ideal for incorporation into various cosmetic vehicles such as creams, lotions, sticks, and soap bars. The coacervated particles provide a dramatic visual effect as well as segregate and protect the entrapped active from the vehicle or environment. The composition is also ideal for incorporation into a hair shampoo formulation where application of the shampoo causes release of the active ingredient from the coacervated particles.

A precipitation polymerization process is used for producing the macroporous cross-linked polymer. In the process, there is polymerized at least one monounsaturated monomer and at least one polyunsaturated monomer in the presence of an organic liquid which is a solvent for and dissolves the monomers but not the polymer. The polymerization of the monomers is initiated by means of a free radical generating catalytic compound, precipitating a polymer in the solvent in the form of a powder. A dry powder is formed by removing the solvent from the precipitated polymeric powder.

The solvent is preferably isoproply alcohol, although ethanol, toluene, heptane, xylene, hexane, ethyl alcohol, and cyclohexane, may also be employed. The monounsaturated monomer and the polyunsaturated monomer can be present in mol ratios of, for example, 20:80, 30:70, 40:50, or 50:50. The process includes the step of stirring the monomers, solvent, and the free radical generating catalytic compound, during polymerization. Preferably, the dry powder is formed by filtering excess solvent from the precipitated powder, and the filtered powder is vacuum dried. The powder may then be "post adsorbed" with various functional materials.

The powders and beads of the present invention may be used as carriers or adsorbents for materials such as water, aqueous systems, emollients, moisturizers, fragrances, dyes, pigments, flavors, drugs such as ibuprofen, phosphoric acid, insect repellents, vitamins, sunscreens, detergents, cosmetics, pesticides, pheromones, herbicides, steroids, sweeteners, pharmaceuticals, and antimicrobial agents. Finely divided solids such as analgesic materials can be adsorbed by dissolving the finely divided analgesic in a solvent, mixing the analgesic and solvent with the powder, and removing the solvent. Other post adsorbable materials include alkanes, alcohols, acid esters, silicones, glycols, organic acids, waxes, and alcohol ethers.

These and other objects, features, and advantages, of the present invention will become apparent when considered in light of the following detailed description, including the accompanying drawings.

In the drawings, the magnification is indicated in each figure. For example, the magnification in FIGS. 6-9 is 1000×, and 2000× in FIG. 10. FIGS. 6-10 also include an insert identifying a length approximating ten microns for comparative purposes.

It should be pointed out, that in viewing the various figures, one will note that as the rate of stirring is increased from zero rpm up to eight hundred rpm, that the size of the unit particles increase. This is in direct opposition to what has been traditionally observed in suspension polymerization systems, wherein increases in stirring rates decrease particle size. Because of the increased size of the unit particles shown in FIG. 10 and the resulting decrease in surface area, the adsorptive capacity of these large particles is less than the adsorptive capacity of the smaller sized particles shown in FIGS. 6-9. The most effective unit particles can be produced if the rate of stirring is maintained below about three hundred rpm, although particles produced at rates beyond three hundred rpm are useful and adsorptive, but to a lesser extent.

DETAILED DESCRIPTION OF THE INVENTION

The material of the present invention, can be broadly and generally described as a crosslinked polymer capable of entrapping solids, liquids, and gases. The polymer is in particulate form and constitutes free flowing discrete solid particles even when loaded with an active material. When loaded, it may contain a predetermined quantity of the active material. One polymer of the invention has the structural formula:

where the ratio of x to y is 80:20, R' is $-CH_2CH_2-$, and R'' is $-(CH_2)_{11}CH_3$.

The polymer is highly crosslinked as evidenced by the foregoing structural formula, and is more particularly a highly crosslinked polymethacylate polymer. This material is manufactured by the Dow Corning Corporation, Midland, Mich., U.S.A., and sold under the trademark POLYTRAP®. It is a low density, highly porous, free-flowing white particulate, and the particles are capable of adsorbing high levels of lipophilic liquids and some hydrophilic liquids, while at the same time maintaining a free-flowing particulate character.

In the powder form, the structure of the particulate is complex, and consists of unit particles less than one micron in average diameter. The unit particles are fused into agglomerates of twenty to eighty microns in average diameter. These agglomerates are loosely clustered into macro-particles termed aggregates of about 200 to about 1200 microns in average diameter.

Adsorption of active ingredients to form post adsorbent powder, can be accomplished using a stainless steel mixing bowl and a spoon, wherein the active ingredient is added to the empty dry powder, and the spoon is used to gently fold the active into the powder. Low viscosity fluids may be adsorbed by addition of the fluids to a sealable vessel containing the powder and tumbling the materials until a consistency is achieved. More elaborate blending equipment such as ribbon or twin cone blenders can also be employed.

The following example illustrates the method for making an absorbent powder, of the type illustrated in FIGS. 1-3 and 6-10.

EXAMPLE I

A hydrophobic porous copolymer was produced by the precipitation polymerization technique by mixing in a five hundred milliliter polymerization reactor equipped with a paddle type stirrer, 13.63 grams of ethylene glycol dimethacylate monomer, or eighty mole percent, and 4.37 grams of lauryl methacrylate monomer, or twenty mole percent. Isopropyl alcohol was added to the reactor as the solvent in the amount of 282 grams. The monomers were soluble in the solvent, but not the precipitated copolymer. The process can be conducted with only polyunsaturated monomers if desired. The mixture including monomers, solvent, and 0.36 grams of catalytic initiator benzoyl peroxide, was purged with nitrogen. The system was heated by a water bath to about sixty degrees Centigrade until copolymerization was initiated, at which time, the temperature was increased to about 70-75 degrees Centigrade for six hours, in order to complete the copolymerization. During this time, the copolymer precipitated from the solution. The copolymerization produced unit particles of a diameter less than about one micron. Some of the unit particles adhered together providing agglomerates of the order of magnitude of about twenty to eighty microns in diameter. Some of the agglomerates adhered further and were fused and welded one to another, forming aggregates of loosely held assemblies of agglomerates of the order of magnitude of about two to eight hundred microns in diameter. The mixture was filtered to remove excess solvent, and a wet powder cake was tray dried in a vacuum oven. A dry hydrophobic copolymeric powder consisting of unit particles, agglomerates, and aggregates was isolated.

The adsorptive capacity of the hydrophobic particulates produced in Example I, as a function of the stirring rate, was determined. The stirring rate during the reaction in Example I significantly influenced the adsorption properties of the particulate materials. The adsorptivity of the particulate materials decreases with an increase in stirring rate, and the density of the particulates increases. These results are set forth in Tables I-III.

TABLE I

| Agitation Rate (RPM) | Bulk Density (g/cc) | Average Aggregate Size (μ) | Average Agglomerate Size (μ) | Average Unit Particle Size (μ) | Adsorption Capacity* |
|---|---|---|---|---|---|
| 0 | 0.067 | 182.5 | 33.9 | 1.0 | 83.0 |
| 75 | 0.077 | 140.6 | 36.6 | 0.5 | 84.8 |
| 150 | 0.071 | 149.8 | 39.8 | 0.8 | 83.0 |
| 300 | 0.293 | 47.0 | 34.0 | 1.5-2.0 | 58.3 |
| 800 | 0.440 | — | 10.0 | 3.0-5.0 | 37.7 |

*Percent Silicone Oil

TABLE II

| Stirring Speed RPM | Adsorption Capacity % | | | |
|---|---|---|---|---|
| | Water | Mineral Oil | Glycerine | Organic Ester* |
| 0 | 0 | 80 | 75 | 80 |
| 75 | 0 | 83.9 | 75 | 81.5 |
| 150 | 0 | 80 | 75 | 80 |
| 300 | 0 | 54.5 | 58.3 | 54.5 |

*2-ethylhexyl-oxystearate

TABLE III

| RPM | Adsorption Capacity % | | | Density (g/cm³) | |
|---|---|---|---|---|---|
| | Mineral Oil | 2-ethylhexyl oxystearate | Silicone Oil | Bulk | Tapped |
| 0 | 82.5 | 82.5 | 86.5 | 0.0368 | 0.0580 |
| 75 | 82.3 | 82.2 | 86.5 | 0.0462 | 0.0667 |
| 150 | 82.3 | 82.3 | 86.3 | 0.0527 | 0.0737 |
| 200 | 81.5 | 81.5 | 85.7 | 0.0554 | 0.0752 |
| 250 | 79.2 | 80.0 | 84.8 | 0.0636 | 0.0859 |
| 300 | 68.8 | 68.8 | 75.0 | 0.1300 | 0.1768 |
| 450 | 58.3 | 58.3 | 61.5 | 0.1736 | 0.2392 |
| 600 | 54.5 | 54.5 | 60 | 0.1933 | 0.2792 |
| 700 | 42.2 | 42.5 | 45.7 | 0.2778 | 0.4142 |
| 800 | 33.3 | 28.6 | 33.3 | 0.3862 | 0.5322 |
| 1000 | 32.8 | 28.5 | 32.9 | 0.3808 | 0.5261 |

In the foregoing tables, it can be seen that adsorption and density, as a function of stirring rate, was determined for several fluids including a silicone oil, water, mineral oil, glycerine, and an organic ester. From zero rpm up to about 250 rpm, the adsorptivity of the porous copolymeric powder particulates of Example I remained essentially consistent. However, at about three hundred rpm, there was a substantial decrease in adsorptivity, which decrease became more apparent as the stirring rate was increased up to about one thousand rpm. A similar pattern is evidenced by the data which are reflective of the density.

This phenomenon is more apparent in the photomicrographic figures of the drawing. Thus, it can be seen from FIG. 6, that the particle size of the unit particles increases as the stirring rate is increased, as evidenced by FIG. 10. A progression in this phenomenon can be observed in FIGS. 7-9.

While the procedure of Example I is a precipitation polymerization process and not a suspension polymerization system, the prior art dealing with suspension polymerization processes, teaches that an increase in stirring rate causes a decrease in particle size. This is documented, for example, in U.S. Pat. No. 4,224,415, issued Sept. 23, 1980, and in the PCT International Publication. The PCT International Publication employs stirring rates upwards of nine hundred to twelve hundred rpm. In Example I of the present invention, however, increases in stirring rates not only did not decrease the particle size, but in fact had exactly the opposite effect, causing the unit particle size to increase. As the rate of stirring increased from zero rpm up to one thousand, the density of the particles increased and the adsorptive capacity decreased.

In accordance with the above, it is possible to tailor porous adsorbent powders of a particular particle size and absorptivity by means of stirring rate. Thus, with large unit particles in FIG. 10, the absorptive capacity is less than the absorptive capacity of smaller sized unit particles in FIGS. 6-9. While the most effective particles are produced when the rate of stirring is maintained below about three hundred rpm, particles produced at rates beyond three hundred rpm are useful.

It is important to understand that the method of Example I for the production of porous polymer particulate powder materials is characterized as a precipitation polymerization technique. In accordance with the technique, monomers are dissolved in a compatible volatile solvent in which both monomers are soluble. Polymer in the form of a powder is precipitated and the polymer is insoluble in the solvent. No surfactant or dispersing aid is required. The materials produced are powders and not spheres or beads. The powder particulates include unit particles, agglomerates, and aggregates. The volatile solvent is subsequently removed resulting in a dry powder, which can be post adsorbed with a variety of functional active ingredients. The suspension polymerization process on the other hand, provides that polymerization be carried out in water, and in some cases chloroform or chlorinated solvents. The monomers, the active, and the catalyst, form beads or droplets in water, and polymerization occurs within each bead. A surfactant or stabilizer, such as polyvinyl pyrrolidone, is required in order to prevent the individually formed beads and droplets from coalescing. The resulting beads, with the active material entrapped therein, include a substantially spherical outer crust or shell, the interior of which contains a macroporous structure. The bead is about ten microns in average diameter to about one hundred-fifty microns, depending upon the rate of agitation employed during the process. Such beads are shown in FIGS. 4 and 5, and the process is set forth in Example III.

Figure 1:
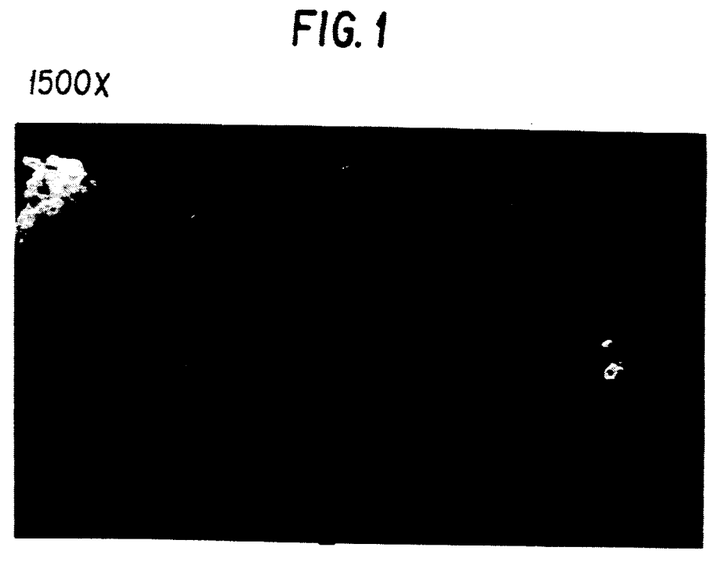
FIG. 1 is a photomicrograph of the various components of the complex structure of the powder produced in Example I, and including unit particles, agglomeratures, and aggregates.
Figure 2:
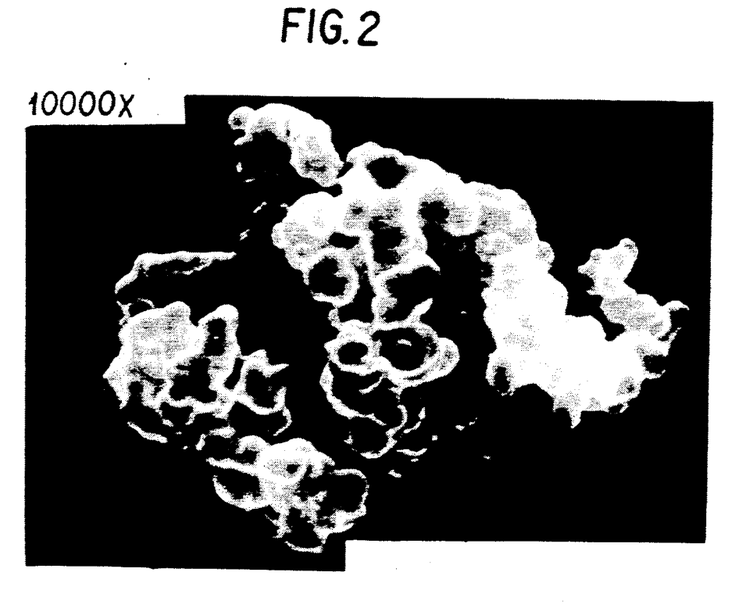
FIGS. 2 and 3 are photomicrographs of the agglomerates and aggregates of FIG. 1, respectively, shown on a larger scale.
Figure 3:
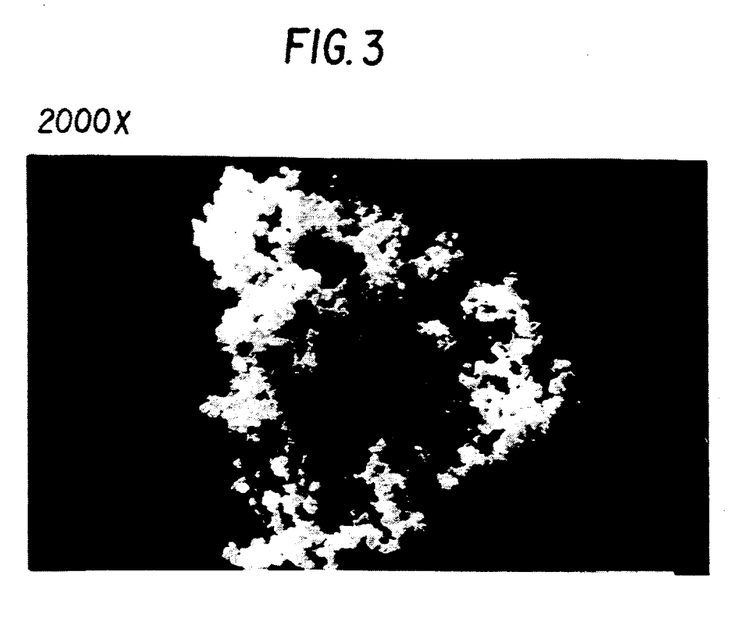
Figure 4:
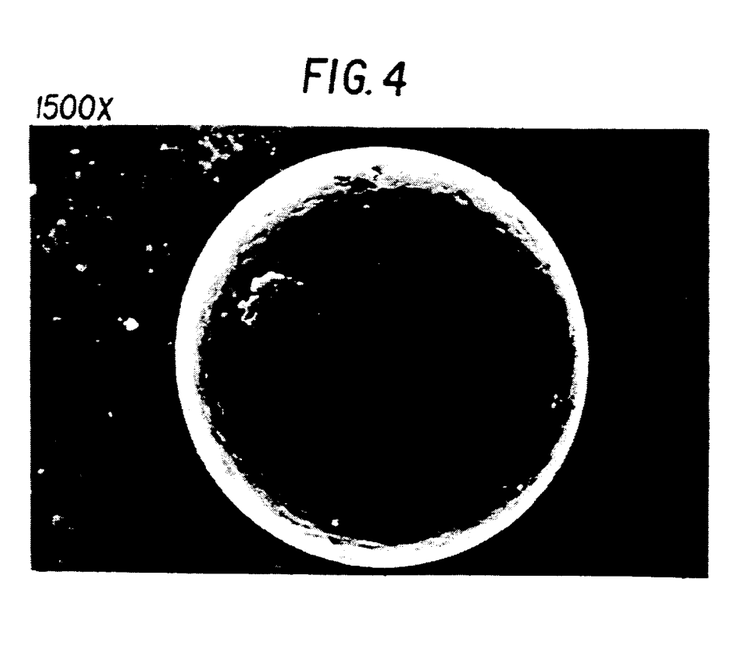
FIG. 4 is a photomicrograph of a polymer bead produced by suspension polymerization in Example III.
Figure 5:
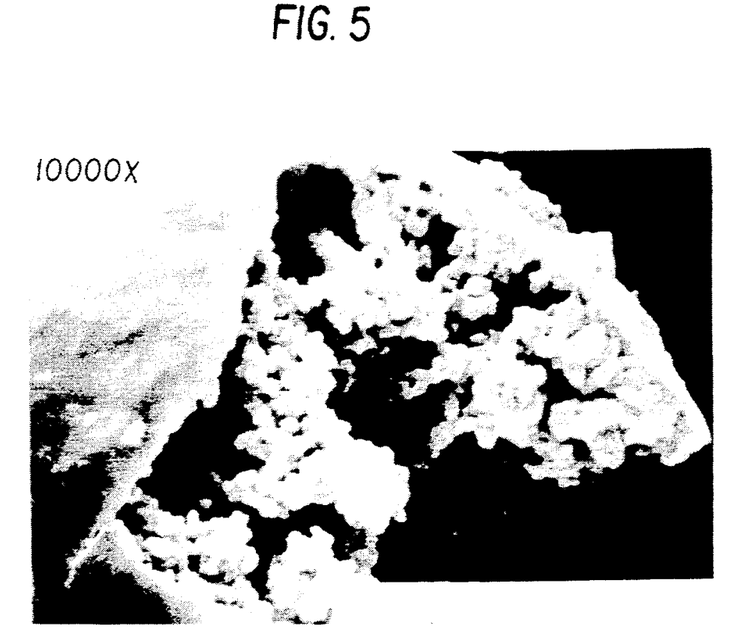
FIG. 5 is a photomicrograph of the bead of FIG. 4 with a portion of the shell removed to reveal the interior structure of the bead.
Figure 6:
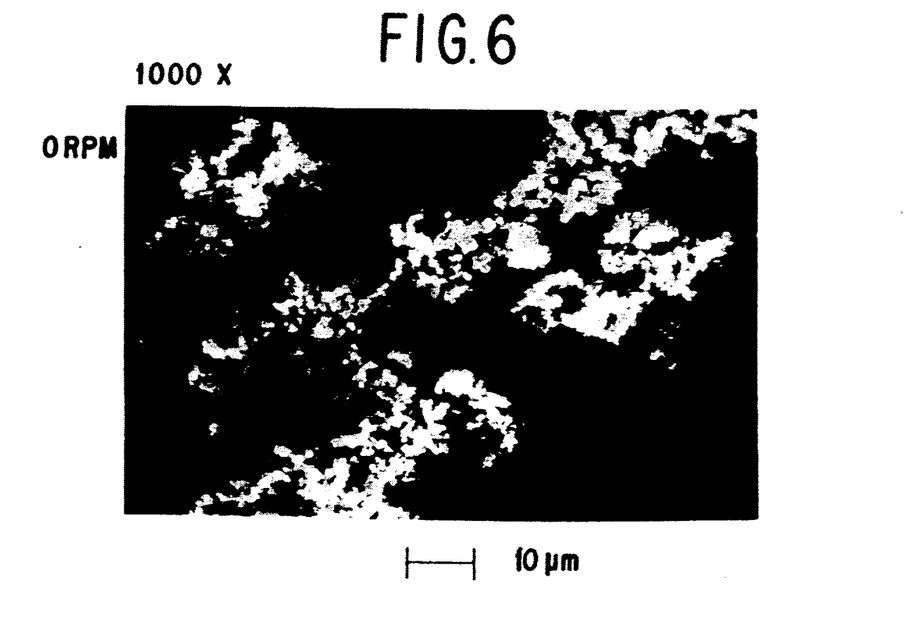
FIG. 6 is a photomicrograph of a polymeric powder material. The powder is shown in magnification as it appears when the agitation rate employed in the process for producing the powder in Example I is zero rpm.
Figure 7:
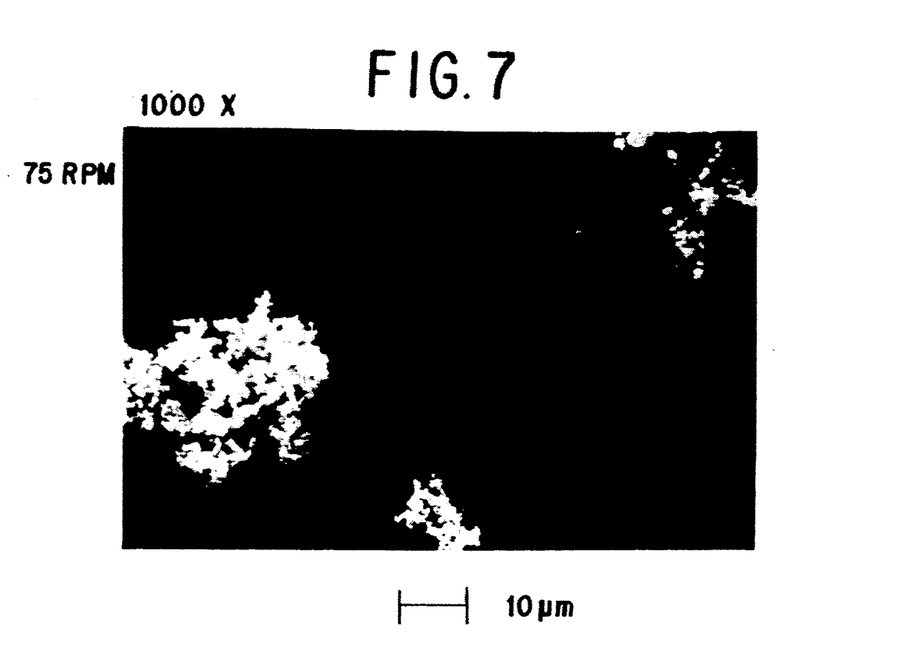
FIGS. 7-10 are additional photomicrographs of polymeric powder materials. The powder is shown in magnification as it appears when the agitation rate employed in the process for producing the powder in Example I varies from seventy-five rpm to eight hundred rpm.
Figure 8:
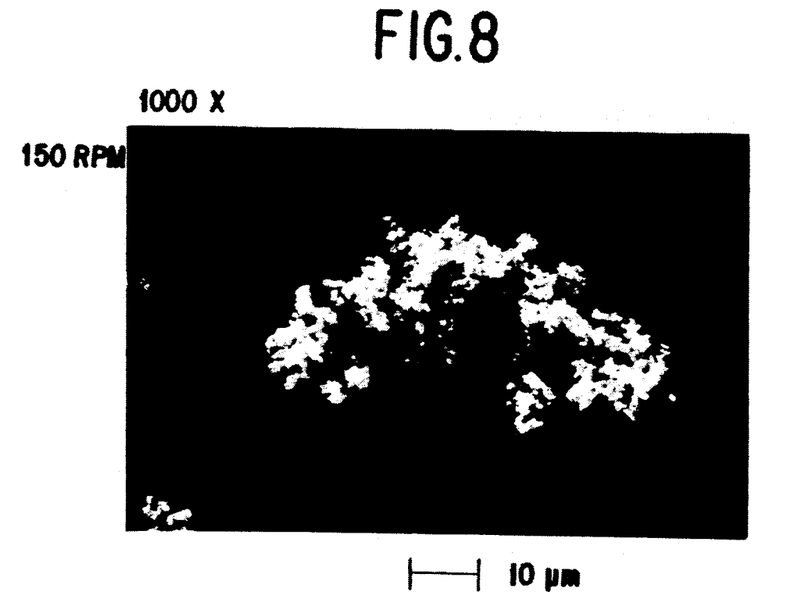
Figure 9:
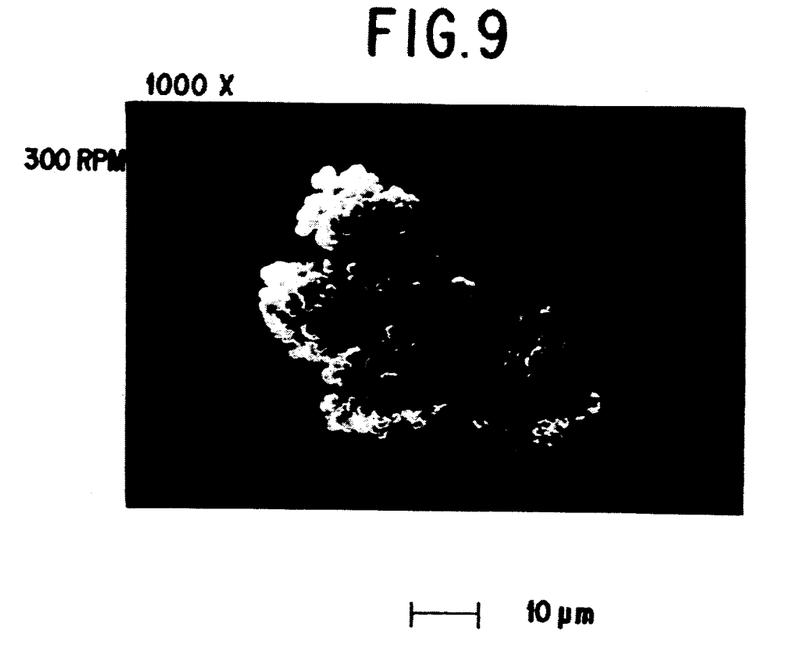
Figure 10:
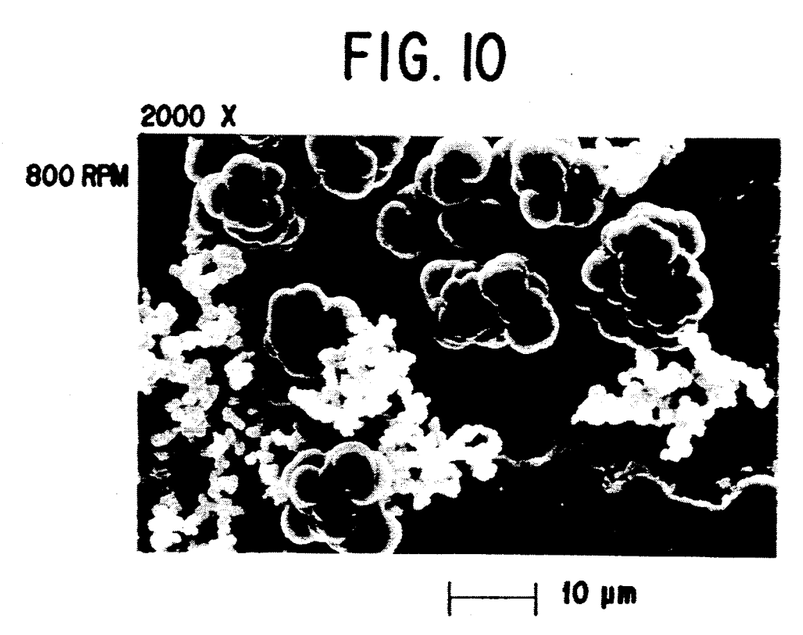

Some unique features of the powders of Example I and FIGS. 1-3 and 6-10 and the bead of Example III and FIGS. 4 and 5 are their ability to adsorb from sixty to eighty percent of a liquid and yet remain free flowing. The materials provide a regulated release of volatile ingredients such as cyclomethicone entrapped therein, and have the capability of functioning as carriers for other non-volatile oils. Loaded powders disappear when rubbed upon a surface. This phenomenon is believed due to the fact that large aggregates of the material scatter light rendering the appearance of a white particulate, however, upon rubbing, these large aggregates decrease in size approaching the range of visible light and hence seem to disappear. The materials find applications in diverse areas such as cosmetics and toiletries, household and industrial products, pesticides, pheromone carriers, and pharmaceuticals. The materials do not swell and are insoluble in common solvents and are capable of physically absorbing active ingredients by the filling of interstitial voids by capillary action. The active ingredients are subsequently released by capillary action or wicking from the voids within the particulates.

The following example illustrates a precipitation polymerization process in which an organic ester is entrapped "in situ" in the polymer powder.

EXAMPLE II 7 grams of 2-ethylhexyl oxystearate was mixed with 1.5 grams of ethylene glycol dimethacrylate and 1.5 grams of lauryl methacrylate in a glass test tube. The solution was deaerated for five (5) minutes and 0.1 ml of t-butyl peroctoate was added and mixed while heating to 80 degrees Centigrade in an oil bath. After 20 minutes, the contents solidified; and the mixture was maintained at about 80 degrees Centigrade for an additional hour to assure full polymerization. A heterogeneous white opaque polymer resulted containing the entrapped ester.

The powder of Example II differs from the powder of Example I in that the solvent in Example I is removed resulting in a dry empty powder which is post adsorbed with other functional materials. The powder of Example II is otherwise similar to the material shown in FIGS. 1–3.

Example III illustrates a process for the production of beads as shown in FIGS. 4 and 5. The process is suspension polymerization and an organic ester is entrapped "in situ".

EXAMPLE III 1.20 grams of polyvinyl pyrrolidone was dissolved in 1500 ml of water in a 2000 ml three necked resin flask equipped with a stirrer, thermometer and nitrogen purge. A solution of 335 grams of 2-ethylhexyl oxystearate, 132 grams ethylene glycol dimethacrylate, 33 grams 2-ethylhexyl methacrylate, and 5 ml t-butyl peroctoate, was bubbled with nitrogen for 5 minutes. The resultant mix was slowly added to the stirred aqueous solution of polyvinyl pyrrolidone at 22 degrees Centigrade under nitrogen. The temperature was raised to 80 degrees Centigrade with constant agitation and held until polymerization started in approximately 15 minutes, and maintained at 80 degrees Centigrade for an additional 2 hours to complete the reaction. White opaque beads were collected by filtering off the supernatant liquid and dried to remove any excess water. The beads weighed 450 g for a yield of 90%, and were 0.25 to 0.5 mm in diameter. Other protective colloids such as starch, polyvinyl alcohol, carboxymethyl cellulose, methyl cellulose, or inorganic systems such as divalent alkali metal hydroxides, for example MgOH, may be used in place of the polyvinyl pyrrolidone suspending medium.

In Example III macroporous polymers submicron in size are produced with two or more monomers, at least one monomer of which contains more than a single double bond. The polymerization is conducted in the presence of an active ingredient which does not dissolve or swell the resulting polymer. The monomers and the active ingredient are mutually soluble, but are insoluble in the aqueous suspending medium in which droplets are formed. Polymerization occurs within suspended droplets, and beads or spheres are produced. The active ingredient which is polymerized "in situ" is entrapped and contained within the beads, but the active ingredient is capable of being released. It is also possible to use a volatile liquid during polymerization, and to subsequently thermally drive off the volatile liquid, leaving behind a porous polymer bead product into which a variety of active materials can be subsequently adsorbed.

Examples of polyunsaturated monomers suitable for use in accordance with the present invention are ethylene glycol dimethacrylate, triethylene glycol dimethacrylate, tetraethylene glycol dimethacrylate, trimethylol propane ethoxylated triacrylate, ditrimethylol propane dimethacrylate; propylene, dipropylene and higher propylene glycols, 1,3 butylene glycol dimethacrylate, 1,4 butanenediol dimethacrylate, 1,6 hexanediol dimethacrylate, neopentyl glycol dimethacrylate, pentaerythritol dimethacrylate, dipentaerythritol dimethacrylate, bisphenol A dimethacrylate, divinyl and trivinyl benzene, divinyl and trivinyl toluene triallyl maleate, triallyl phosphate, diallyl maleate, diallyl itaconate, and allyl methacrylate. The monounsaturated monomers include allyl methacrylates and acrylates having straight or branched chain alkyl groups with 1 to 30 carbon atoms, preferably 5 to 18 carbon atoms. Preferred monomers include lauryl methacrylate, 2-ethylhexyl methacrylate, isodecylmethacrylate, stearyl methacrylate, hydroxy ethyl methacrylate, hydroxy propyl methacrylate, diacetone acrylamide, phenoxy ethyl methacrylate, tetrahydrofurfuryl methacrylate and methoxy ethyl methacrylate.

As noted previously, the polymer can be formed by copolymerizing one monounsaturated monomer with one polyunsaturated monomer, or with only polyunsaturated monomers.

EXAMPLE IV

Example I was repeated for each of a series of monomer systems shown in Tables IV–XVII. In each instance, submicron sized polymeric powders were produced employing a stirring speed of about seventy-five RPM. The catalyst was benzoyl peroxide. Adsorption capacities of the various polymeric powders for fluids were determined and are shown in the Tables, along with the mole ratios of monomers and the solvent. The abbreviations used in Tables IV–XVII are identified as follows:

| | |
|---|---|
| DAA | Diacetone acrylamide |
| EGDM | Ethylene gylcol dimethacrylate |
| TEGDM | Tetraethylene glycol dimethacrylate |
| ST | Styrene |
| DVB | Divinylbenzene |
| VP | Vinyl pyrrolidone |
| IBOMA | Isobornyl methacrylate |
| PEMA | Phenoxyethyl methacrylate |
| IDMA | Isodecyl methacrylate |
| STMA | Stearyl methacrylate |
| HPMA | Hydroxypropyl methacrylate |
| CYMA | Cyclohexyl methacrylate |
| DMAEMA | Dimethylaminoethyl methacrylate |
| TBAEMA | t-butyl aminoethyl methacrylate |
| AMPS | 2-acrylamido propane sulfonic acid |
| BMA | Butyl methacrylate |
| EHMA | 2-ethylhexyl methacrylate |
| MMA | Methyl methacrylate |
| HEMA | 2-hydroxyethyl methacrylate |
| EHO | 2-ethylhexyl oxystearate |
| GG | Glucose glutamate |
| IPA | Isopropyl alcohol |
| PEG | Polyethylene glycol 200 |

TABLE IV

| Monomers | Mole Ratio | Solvent | Adsorption Capacity % | | | |
|---|---|---|---|---|---|---|
| | | | EHO | Glycerine | GG | Water |
| DAA/EGDM | 20/80 | Xylene | 75 | 82 | 83 | 78 |
| DAA/EGDM | 30/70 | Xylene | 77 | 80 | 83 | 78 |
| DAA/EGDM | 40/60 | Xylene | 75 | 75 | 83 | 77 |
| DAA/EGDM | 50/50 | Xylene | 50 | 57 | 67 | 0 |
| DAA/EGDM | 60/40 | Xylene | 40 | 40 | 50 | 0 |
| DAA/TEGDM | 20/80 | Xylene | 40 | 50 | 62 | 58 |
| DAA/TEGDM | 30/70 | Xylene | 29 | 40 | 50 | 55 |
| DAA/TEGDM | 40/60 | Xylene | 25 | 28 | 40 | 43 |
| DAA/TEGDM | 50/50 | Xylene | 25 | 30 | 40 | 43 |
| DAA/TEGDM | 60/40 | Xylene | 22 | 29 | 40 | 40 |

TABLE V

| Monomers | Mole Ratio | Solvent | Adsorption Capacity % | | | |
|---|---|---|---|---|---|---|
| | | | EHO | Glycerine | PEG | Water |
| ST/TEGDM | 20/80 | IPA | 58 | 69 | 69 | 67 |
| ST/TEGDM | 30/70 | IPA | 58 | 64 | 67 | 69 |
| ST/TEGDM | 40/60 | IPA | 62 | 71 | 71 | 61 |
| ST/TEGDM | 50/50 | IPA | 67 | 62 | 54 | 58 |
| ST/TEGDM | 60/40 | IPA | 50 | 58 | 58 | 54 |
| ST/TEGDM | 70/30 | IPA | 50 | 58 | 50 | 54 |
| ST/TEGDM | 80/20 | IPA | 44 | 54 | 50 | 50 |
| ST/DVB | 20/80 | IPA | 80 | 75 | 75 | 0 |
| ST/DVB | 30/70 | IPA | 75 | 67 | 75 | 0 |
| ST/DVB | 40/60 | IPA | 69 | 67 | 67 | 0 |
| ST/DVB | 50/50 | IPA | 64 | 72 | 67 | 0 |
| ST/DVB | 60/40 | IPA | 67 | 71 | 71 | 0 |
| ST/DVB | 70/30 | IPA | 71 | 75 | 76 | 0 |
| ST/DVB | 80/20 | IPA | 50 | 50 | 50 | 0 |

TABLE VI

| Monomers | Mole Ratio | Solvent | Adsorption Capacity % | | | |
|---|---|---|---|---|---|---|
| | | | EHO | Glycerine | GG | Water |
| VP/EGDM | 20/80 | Xylene | 77 | 80 | 74 | 73.6 |
| VP/EGDM | 30/70 | Xylene | 76 | 79 | 78.3 | 70 |
| VP/EGDM | 40/60 | Xylene | 70 | 67 | 75.6 | 75 |
| VP/EGDM | 50/50 | Xylene | 72 | 76 | 80 | 76 |
| VP/EGDM | 60/40 | Xylene | 74 | 80 | 76 | 77 |
| VP/EGDM | 70/30 | IPA | 71 | 78 | 74 | 75 |
| VP/EGDM | 80/20 | IPA | 67 | 75 | 73 | 74 |
| VP/TEGDM | 20/80 | Xylene | 58 | 68.8 | 61.5 | 67.7 |
| VP/TEGDM | 30/70 | Xylene | 70 | 67 | 54.5 | 68.8 |
| VP/TEGDM | 40/60 | Xylene | 54.5 | 61.5 | 52.4 | 64.3 |
| VP/TEGDM | 50/50 | Xylene | 44.4 | 47.4 | 52.4 | 52.4 |
| VP/TEGDM | 60/40 | Xylene | 50 | 44.4 | 50 | 54.4 |
| VP/TEGDM | 70/30 | Xylene | 50 | 47.4 | 44.4 | 50 |
| VP/TEGDM | 80/20 | Xylene | 54.5 | 52.4 | 60 | 58 |

TABLE VII

| Monomers | Mole Ratio | Solvent | Adsorption Capacity % | | | |
|---|---|---|---|---|---|---|
| | | | EHO | Glycerine | GG | Water |
| IBOMA/EGDM | 20/80 | IPA | 62.9 | 9.1 | 71.4 | 0 |
| IBOMA/EGDM | 30/70 | IPA | 64.3 | 16.6 | 67.7 | 0 |
| IBOMA/EGDM | 40/60 | IPA | 68.7 | 28.6 | 61.5 | 0 |
| IBOMA/EGDM | 50/50 | IPA | 67.7 | 16.7 | 58.3 | 0 |
| IBOMA/EGDM | 60/40 | IPA | 50 | 23.1 | 50 | 0 |
| IBOMA/EGDM | 70/30 | IPA | 50 | 9.1 | 47.3 | 0 |
| IBOMA/EGDM | 80/20 | IPA | 52.3 | 16.6 | 44.4 | 0 |
| IBOMA/TEGDM | 20/80 | IPA | 66.6 | 62.9 | 61.5 | 0 |
| IBOMA/TEGDM | 30/70 | IPA | 61.5 | 61.5 | 70.6 | 0 |
| IBOMA/TEGDM | 40/60 | IPA | 64.3 | 64.3 | 71.4 | 0 |
| IBOMA/TEGDM | 50/50 | IPA | 61.5 | 66.6 | 67.7 | 0 |
| IBOMA/TEGDM | 60/40 | IPA | 58.3 | 54.5 | 54.5 | 0 |
| IBOMA/TEGDM | 70/30 | IPA | 47.3 | 50 | 41.1 | 0 |
| IBOMA/TEGDM | 80/20 | IPA | 37.5 | 41.1 | 33.3 | 0 |

TABLE VIII

| Monomers | Mole Ratio | Solvent | Adsorption Capacity % | | | |
|---|---|---|---|---|---|---|
| | | | EHO | Glycerine | GG | Water |
| PEMA/EGDM | 20/80 | IPA | 64.3 | 68.7 | 66.6 | 61.5 |
| PEMA/EGDM | 30/70 | IPA | 54.5 | 50 | 54.5 | 44.4 |
| PEMA/EGDM | 40/60 | IPA | 52.3 | 47.3 | 72.2 | 9 |
| PEMA/EGDM | 50/50 | IPA | 54.5 | 33.3 | 62.9 | 0 |
| PEMA/EGDM | 60/40 | IPA | 67.7 | 28.5 | 70.5 | 0 |
| PEMA/EGDM | 70/30 | IPA | 69.7 | 44.4 | 60.7 | 0 |
| PEMA/EGDM | 80/20 | IPA | 66.6 | 68.7 | 66.6 | 0 |
| PEMA/TEGDM | 20/80 | IPA | 58.3 | 56.5 | 66.6 | 58.3 |
| PEMA/TEGDM | 30/70 | IPA | 64.2 | 70.5 | 67.7 | 62.9 |
| PEMA/TEGDM | 40/60 | IPA | 66.6 | 67.7 | 71.4 | 69.7 |
| PEMA/TEGDM | 50/50 | IPA | 66.6 | 70.5 | 73.6 | 72.2 |
| PEMA/TEGDM | 60/40 | IPA | 58.3 | 62.9 | 52.3 | 61.5 |
| PEMA/TEGDM | 70/30 | IPA | 50 | 58.3 | 52.3 | 54.5 |
| PEMA/TEGDM | 80/20 | IPA | 67.7 | 73.6 | 76.1 | 47.3 |

TABLE IX

| Monomers | Mole Ratio | Solvent | Adsorption Capacity % | | | |
|---|---|---|---|---|---|---|
| | | | EHO | Glycerine | PEG | Water |
| IDMA/EGDM | 20/80 | IPA | 55 | 64 | 70 | 0 |
| IDMA/EGDM | 30/70 | IPA | 38 | 50 | 44 | 0 |
| IDMA/EGDM | 40/60 | IPA | 50 | 67 | 69 | 0 |
| IDMA/EGDM | 50/50 | IPA | 58 | 64 | 67 | 0 |
| IDMA/EGDM | 60/40 | IPA | 58 | 69 | 69 | 0 |
| IDMA/TEGDM | 20/80 | IPA | 62 | 70 | 70 | 0 |
| IDMA/TEGDM | 30/70 | IPA | 50 | 62 | 62 | 0 |
| IDMA/TEGDM | 40/60 | IPA | 62 | 67 | 67 | 0 |
| IDMA/TEGDM | 50/50 | IPA | 38 | 44 | 50 | 0 |
| IDMA/TEGDM | 60/40 | IPA | 38 | 55 | 50 | 0 |

TABLE X

| Monomers | Mole Ratio | Solvent | Adsorption Capacity % | | | |
|---|---|---|---|---|---|---|
| | | | EHO | Glycerine | PEG | Water |
| STMA/EGDM | 10/90 | IPA | 66 | 64.3 | 66.7 | 0 |
| STMA/EGDM | 20/80 | IPA | 69 | 63 | 65.5 | 0 |
| STMA/EGDM | 30/70 | IPA | 73–75 | 58.3 | 61.5 | 0 |
| STMA/EGDM | 40/60 | IPA | 69–71 | 54.5 | 58.3 | 0 |
| STMA/EGDM | 50/50 | IPA | 60–63 | 52.4 | 52.4 | 0 |
| STMA/TEGDM | 20/80 | IPA | 50 | 47.4 | 52.4 | 0 |
| STMA/TEGDM | 30/70 | IPA | 50 | 64.3 | 50 | 0 |
| STMA/TEGDM | 40/60 | IPA | 52.4 | 61.5 | 68.3 | 0 |
| STMA/TEGDM | 50/50 | IPA | 47.4 | 52.4 | 56.5 | 0 |

TABLE XI

| Monomers | Mole Ratio | Solvent | Adsorption Capacity % | | | |
|---|---|---|---|---|---|---|
| | | | EHO | Glycerine | PEG | Water |
| HPMA/EGDM | 20/80 | Xylene | 64.3 | 61.5 | 61.5 | 9 |
| HPMA/EGDM | 30/70 | Xylene | 54.5 | 16.7 | 58.3 | 0 |
| HPMA/EGDM | 40/60 | Xylene | 54.5 | 9 | 58.3 | 0 |
| HPMA/EGDM | 50/50 | Xylene | 37.5 | 58.3 | 50 | 0 |
| HPMA/EGDM | 60/40 | Xylene | 44.4 | 61.5 | 58.3 | 0 |
| HPMA/EGDM | 70/30 | Xylene | 50 | 44.4 | 37.5 | 0 |
| HPMA/EGDM | 80/20 | Xylene | 61.5 | 16.7 | 58.3 | 0 |
| HPMA/TEGDM | 20/80 | Xylene | 50 | 58.3 | 54.5 | 61.5 |
| HPMA/TEGDM | 30/70 | Xylene | 56.5 | 54.5 | 50 | 60 |
| HPMA/TEGDM | 40/60 | Xylene | 50 | 58.3 | 52.4 | 54.5 |
| HPMA/TEGDM | 50/50 | Xylene | 52.4 | 61.5 | 54.5 | 56.5 |
| HPMA/TEGDM | 60/40 | Xylene | 33.3 | 47.4 | 44.4 | 54.5 |
| HPMA/TEGDM | 70/30 | Xylene | 54.5 | 44.4 | 54.5 | 50 |
| HPMA/TEGDM | 80/20 | Xylene | 50 | 47.4 | 41.2 | 37.5 |

TABLE XII

| Monomers | Mole Ratio | Solvent | Adsorption Capacity % | | | |
|---|---|---|---|---|---|---|
| | | | EHO | Glycerine | PEG | Water |
| CYMA/EGDM | 80/20 | IPA | 61.5 | 71.4 | 66.6 | 0 |
| CYMA/EGDM | 70/30 | IPA | 60 | 66 | 64.2 | 0 |
| CYMA/EGDM | 60/40 | IPA | 61.5 | 66 | 66.6 | 0 |
| CYMA/EGDM | 50/50 | IPA | 64.2 | 66 | 68.7 | 0 |
| CYMA/EGDM | 40/60 | IPA | 64.2 | 66 | 68.7 | 0 |
| CYMA/EGDM | 30/70 | IPA | 61.5 | 66 | 66.6 | 0 |
| CYMA/EGDM | 20/80 | IPA | 66.6 | 71.4 | 75 | 61.5 |
| CYMA/TEGDM | 80/20 | IPA | 68.7 | 0 | 68.7 | 0 |
| CYMA/TEGDM | 70/30 | IPA | 71.4 | 0 | 69.7 | 0 |
| CYMA/TEGDM | 60/40 | IPA | 66.6 | 0 | 62.9 | 0 |
| CYMA/TEGDM | 50/50 | IPA | | 0 | | 0 |
| CYMA/TEGDM | 40/60 | IPA | 60 | 0 | 72.9 | 0 |

TABLE XII-continued

| Monomers | Mole Ratio | Solvent | Adsorption Capacity % | | | |
|---|---|---|---|---|---|---|
| | | | EHO | Glycerine | PEG | Water |
| CYMA/TEGDM | 30/70 | IPA | 64.2 | 0 | 72.2 | 0 |
| CYMA/TEGDM | 20/80 | IPA | 61.5 | 0 | 66.6 | 0 |

TABLE XIII

| Monomers | Mole Ratio | Solvent | Adsorption Capacity % | | | |
|---|---|---|---|---|---|---|
| | | | Water | Mineral Oil | Glycerine | EHO |
| DMAEMA/EGDM | 20/80 | Hexane | 0 | 58.3 | 66.7 | 58.3 |
| DMAEMA/EGDM | 40/60 | Hexane | 66.7 | 61.5 | 70.6 | 66.7 |
| DMAEMA/EGDM | 60/40 | Hexane | 77.3 | 61.5 | 72.2 | 76.2 |
| DMAEMA/EGDM | 80/20 | Hexane | 66.7 | 58.3 | 68.8 | 58.3 |
| TBAEMA/EGDM | 20/80 | Hexane | 0 | 70.6 | 75 | 70.6 |
| TBAEMA/EGDM | 40/60 | Hexane | 0 | 66.7 | 72.2 | 66.7 |
| TBAEMA/EGDM | 60/40 | Hexane | 0 | 61.5 | 68.75 | 61.5 |
| TBAEMA/EGDM | 80/20 | Hexane | 0 | 44.4 | 54.6 | 50 |
| TBAEMA/EGDM | 80/20 | Hexane | 54.6 | 54.6 | 58.3 | 50 |

TABLE XIV

| Monomers | Mole Ratio | Solvent | Adsorption Capacity % | | | |
|---|---|---|---|---|---|---|
| | | | Water | Mineral Oil | Glycerine | EHO |
| AMPS/EGDM | 20/80 | Xylene | 84.3 | 83.3 | 85.3 | 83.3 |
| BMA/EGDM | 20/80 | Hexane | 0 | 70.6 | 75 | 68.8 |
| BMA/EGDM | 40/60 | Hexane | 0 | 70.6 | 77.3 | 70.6 |
| BMA/EGDM | 40/60 | Ethyl Alcohol | 0 | 66.7 | 73.7 | 68.8 |
| BMA/EGDM | 60/40 | Hexane | 0 | 72.2 | 0 | 73.7 |
| BMA/EGDM | 80/20 | Hexane | 0 | 54.5 | 66.7 | 58.3 |

TABLE XV

| Monomers | Mole Ratio | Solvent | Adsorption Capacity % | | | |
|---|---|---|---|---|---|---|
| | | | Water | Mineral Oil | Glycerine | EHO |
| 2 EHMA/EGDM | 20/80 | IPA | 0 | 68.8 | 66.7 | 64.3 |
| 2 EHMA/EGDM | 30/70 | IPA | 0 | 68.8 | 66.7 | 64.3 |
| 2 EHMA/EGDM | 40/60 | IPA | 0 | 66.7 | 66.7 | 70.6 |
| 2 EHMA/EGDM | 50/50 | IPA | 0 | 64.3 | 68.3 | 61.5 |
| 2 EHMA/EGDM | 60/40 | IPA | 0 | 61.5 | 64.3 | 50 |
| 2 EHMA/EGDM | 70/30 | IPA | 0 | 58.3 | 64.3 | 50 |
| 2 EHMA/EGDM | 80/20 | IPA | 0 | 58.3 | 64.3 | 50 |

TABLE XVI

| Monomers | Mole Ratio | Solvent | Adsorption Capacity % | | | |
|---|---|---|---|---|---|---|
| | | | Water | Mineral Oil | Glycerine | EHO |
| MMA/EGDM | 20/80 | IPA | 61.5 | 58.3 | 64.3 | 58.3 |
| MMA/EGDM | 30/70 | IPA | 64.3 | 61.5 | 66.7 | 61.5 |
| MMA/EGDM | 40/60 | IPA | 61.5 | 64.3 | 64.3 | 61.5 |
| MMA/EGDM | 50/50 | IPA | 58.3 | 54.5 | 61.5 | 58.3 |
| MMA/EGDM | 60/40 | IPA | 54.5 | 50 | 61.5 | 54.5 |
| MMA/EGDM | 70/30 | IPA | 66.7 | 61.5 | 72.2 | 64.3 |
| MMA/EGDM | 80/20 | IPA | 66.7 | 44.4 | 78.3 | 44.4 |

TABLE XVII

| Monomers | Mole Ratio | Solvent | Adsorption Capacity % | | | |
|---|---|---|---|---|---|---|
| | | | Water | PEG | Glycerine | EHO |
| HEMA/EGDM | 20/80 | IPA | 54.5 | 54.5 | 54.5 | 50 |
| HEMA/EGDM | 30/70 | IPA | 58.3 | 64.3 | 58.3 | 54.5 |
| HEMA/EGDM | 40/60 | IPA | 58.3 | 61.5 | 64.3 | 54.5 |
| HEMA/EGDM | 50/50 | IPA | 61.5 | 61.5 | 61.5 | 50 |
| HEMA/EGDM | 60/40 | IPA | 61.5 | 64.3 | 61.5 | 50 |
| HEMA/EGDM | 70/30 | IPA | 58.3 | 64.3 | 58.3 | 50 |

TABLE XVII-continued

| Monomers | Mole Ratio | Solvent | Adsorption Capacity % | | | |
|---|---|---|---|---|---|---|
| | | | Water | PEG | Glycerine | EHO |
| HEMA/EGDM | 80/20 | IPA | 61.5 | 58.3 | 61.5 | 54.5 |

As noted above, highly crosslinked, polymeric systems consisting of particles of submicron size, can be prepared from monomers having at least two polymerizable unsaturated bonds and containing no comonomers having monounsaturated moiety. These highly crosslinked systems can adsorb large quantities of active substances even of very different structures and properties. Examples of such monomers are bis or poly acrylates, methacrylates or itaconates of ethylene glycol, propylene glycol, di-, tri-, tetra-, poly- ethylene glycol and propylene glycol, trimethylol propane, glycerine, erythritol, xylitol, pentaerythritol, di-pentaerythritol, sorbitol, mannitol, glucose, sucrose, cellulose, hydroxy cellulose, methyl cellulose, and 1,2; and 1,3-propanediol, 1,3; and 1,4-butanediol, 1,6-hexanediol, 1,8-octanediol, and cyclohexanediol, and triol. Similarly, bis acrylamido or methacrylamido compounds can be used, such as methylene bis acryl or methacrylamide, 1,2-dihydroxy ethylene bis-acryl or methacrylamide, and hexamethylene bis-acryl or methacrylamide. Another group of monomers are represented by di or poly vinyl esters such as divinyl oxalate, malonate, succinate glutarate, adipate, sebacate, divinyl maleate, fumarate, citraconate, and mesaconate.

Still another group of monomers is represented by di or poly vinyl ethers of ethylene, propylene, butylene, glycols of glycerine, pentaerythritol, sorbitol, divinyl ether, di or poly-allyl compounds based on glycols, and glycerine, or combinations of vinyl allyl or vinyl acryloyl compounds such as vinyl methacrylate, acrylate, allyl methacrylate, acrylate, and methallyl methacrylate, acrylate. Aromatic, cycloaliphatic or heterocyclic monomers such as divinyl benzene, toluene, diphenyl, cyclohexane, trivinyl benzene, divinyl pyridine, and piperidine, can also be used.

The polymerization is achieved by the use of a variety of free radical initiators which can be azo compounds, a peroxy dicarbonate, a peroxy ester, or a sulfonyl acid peroxide. Illustrative of free radical initiators in the process are 2,2'-azobis(2,4-dimethyl-4-methoxy valeronitrile), benzoyl peroxide, 2,2'-azobis-(2,4-dimethylvaleronitrile), 2,2'-azobis (isobutyronitrile), 2-t-butylazo-2-cyano-4-methoxy-4-methylpentane, acetyl peroxide, 2-t-butylazo-2-cyano-4-methylpentane, 2,4-dichlorobenzoyl peroxide, p-chlorobenzoyl peroxide, decanoyl peroxide, diisononanyl peroxide, lauroyl peroxide, propinoyl peroxide, bis(4-t-butyl cyclohexyl) peroxy dicarbonate, di(sec-butyl) peroxy dicarbonate, diisopropyl peroxy carbonate, di(n-propyl) peroxy carbonate, di(2-ethylhexyl) peroxy carbonate, di(2-phenoxyethyl) peroxy carbonate, t-amyl peroxy pivatate, t-amyl perpivatate, t-butyl peroxyacetate, t-butyl peroxyisobutyrate, t-butyl peroxypivalate, t-butyl peroxy neodecanonate, t-amyl perneodecanonate, cumyl perneodecanonate, cumyl perpivate, 2,5-dimethyl-2,5-bis(2-ethyl hexanoyl peroxy) hexane, t-butylperoxy-2-ethylhexanoate, t-amyl peroxy (2-ethylhexanoate) and acetyl cyclohexyl sulfonyl peroxide.

Illustrative redox initiators are methylbutyl amine, bis(2-hydroxyethyl)butyl amine, butyldimethyl amine, dimethyl amine, dibenzylethyl amine, diethylmethyl amine, dimethylpentyl amine, diethyl amine, 2,2',2"-trihydroxy dipropyl ethyl amine, di-n-propylene amine, 2,2',2"-trimethyl tributyl amine, triethyl amine, dimethyl aminoacetal, pentylhexyl amine, triethanolamine, trihexyl amine, trimethyl amine, trioctadecyl amine, tripropyl amine, trisopropyl amine, tetramethylene diamine, and esters of para-amino benzoic acid, e.g., p-dimethyl amino-2-ethylhexyl-benzoate, dimethyl aminoethyl acetate, 2-(n-butoxy)ethyl 4-dimethylaminobenzoate, 2-(dimethylamino) ethyl benzoate, ethyl-4 dimethylaminobenzoate, methyldiethanolamine, dibutyl amine, N,N-dimethylbenzylamine, methylethyl amine and dipentyl amine.

For purposes of the present invention, the term "coacervate" and "coacervating agent" is intended to define a material which causes particles of a predetermined size to collect and form in denser clusters of particles of an increased size. For example, active ingredients are initially entrapped in the powder of FIGS. 1–3 and 6–10 forming particles in the range of 200–1200 microns. These particles containing the entrapped active ingredient are then mixed with a coacervating agent to form much larger particles well in excess of twelve hundred microns. The preferred range of the coacervated particle size is from about 0.2–5.0 millimeters in average diameter. A preferable range is 0.4–2.0 millimeters, although the particles can be as large as one-quarter of an inch in average diameter, if desired. Similarly, active ingredients are first entrapped in the bead form of the invention as shown in FIGS. 4 and 5 forming particles in the range of 10–150 microns. These particles containing the entrapped active ingredient can then be mixed with a coacervating agent to form much larger particles well in excess of one hundred-fifty microns.

Typically of the coacervating agents which may be employed in accordance with the present invention are waxes, gums, resins, polymers, starches, and elastomers. Exemplary of waxes are insect and animal waxes such as beeswax and spermaceti; vegetable waxes such as candelilla, carnauba, Japan wax, Ouricury, Douglas-fir bark wax, rice-bran wax, jojoba, castor wax, and bayberry wax; mineral waxes such as montan wax, peat waxes, ozokerite, and ceresin; petroleum waxes such as paraffin wax; synthetic waxes such as polyethylene waxes, Fischer-Tropsch waxes, chemically modified hydrocarbon waxes, substituted amide waxes; and silicone wax. Reference may be had to U.S. Pat. No. 3,395,169, issued Jul. 30, 1968, describing a silicone wax which is an organosilicon block copolymer; and U.S. Pat. No. 3,563,941, issued Feb. 16, 1971, describing a silicone-carnauba wax copolymer; each patent of which is incorporated herein by reference. In addition, the coacervating agent may include starches; gums such as celullosic gums and alignate gums; polymers such as polyvinyl alcohol; and resins such as polyvinylpyrrolidone.

The active ingredient may be any of the various active materials noted previously in detail. Thus, the active ingredient may include silicones; fatty alcohols such as lauryl, stearyl, and cetyl alcohol; fatty acids such as oleic, stearic, and behenic acid; esters such as isopropyl myristate, isopropyl palmitate, and adipates; lanolin compounds such as acids, alcohols and ethoxylates; natural oils such as mink, jojoba, and wheat germ; fragrances; flavors; pigments; dyes; sunscreens such as octylmethoxy cinnamates, and p-aminobenzoic acid derivatives; botanicals; extracts; cationic compounds and quaternary compounds such as benzalkonium chloride; antimicrobials; and various glycols.

Thus, in accordance with the present invention there is provided macroporous polymer particles entrapping an active ingredient, which particles are in turn formed into multiple and larger particles which are held together or coacervated by a coacervating agent. The coacervated particles find application in various vehicles such as hair shampoo formulations where the function of the coacervated particles is to provide a visual impact because of their large size, and in addition the coacervated particles are capable of releasing the active ingredient when the shampoo is applied. In a particular application, an active ingredient such as a silicone skin conditioner is loaded and entrapped into a macroporous polymer and coacervated to form larger particles. Depending upon the nature of the coacervant selected, the larger particles can vary from abrasive coacervated particles which may be used to slough skin, to soft particles which rub out easily upon application to the skin releasing the active ingredient. While the macroporous particles themselves possess an inherent protecting function with respect to the active ingredient by virtue of entrapping the active ingredient therein, the coacervating agent also functions in protecting the active ingredient when coacervated particles containing the active ingredient are dispersed in vehicles that would under normal circumstances leach out the active ingredient from the macroporous polymer.

The following illustrates the foregoing concepts of the present invention and sets forth a typical formulation for a clear water gel personal care product containing coacervated particles entrapping an emollient.

TABLE I

| FORMULATION | |
|---|---|
| INGREDIENT | WEIGHT PERCENT |
| CARBOPOL ® 940 | 10.0 |
| Triethanolamine | 7.5 |
| Germaben | 0.2 |
| Glycereth 26 | 1.0 |
| Wax Coacervated porous polymer entrapping cyclomethicone | 1.0 |
| Water | 80.3 |
| Dye | — |

In Table I, CARBOPOL is a registered trademark of B.F. Goodrich Chemical Group, Cleveland, Ohio, and a water soluble vinyl polymer which functions as a viscosity builder in the formulation. This viscosity builder is employed as a three percent solution. The formulation is neutralized with triethanolamine which is used as a ten percent solution. Germaben is the designation assigned by the Cosmetics, Toiletries, and Fragrances Association, for the compound selected as a preservative. Glycereth functions in the formulation as an emulsifier and is a polyethylene glycol ether of glycerin having an ethoxylation value of twenty-six. A dye, preferably D&C Green No. 6, is included in the formulation in an amount sufficient to produce a colored visual effect. Cyclomethicone is the Cosmetics, Toiletries, and Fragrances Association designation for polydimethylcyclosiloxane fluid. The cyclosiloxane fluid has the formula $(CH_3)_2SiO_x$ where x is an integer that can vary from three to eight. These cyclosiloxane fluids have vicosities ranging from about two to about six Centistokes measured at twenty-five degrees Centigrade. Such silicone fluids have utility as base fluids in a variety of personal care products, and are useful as ingredients in a range of cosmetic and personal care formulations.

In the formulation of Table I, the coacervated polymer particles which entrap the silicone emollient may be produced employing either the powder particles of Examples I and II, or the bead form of the particles produced in Example III. These particles are coacervated by mixing the particles with a melted coacervating agent and cooling the mixture. For example, in Table I, the coacervated component of the formulation includes about twenty-five percent by weight of the powder particles of Example I, about thirty percent by weight of cyclomethicone entrapped in the powder particles, about forty-four percent by weight of a silicone wax coacervating agent, and one-half of one percent by weight of D&C Green No. 6 color additive. Preferred ranges of the coacervated components based on percent by weight are from 10–70 percent for the coacervating agent, 10–50 percent for the polymer particles, and 5–80 percent for the active ingredient.

Examples V and VI illustrate procedures for producing coacervated macroporous active ingredient entrapped polymer particles in accordance with the present invention. These procedures are suitable for the production of coacervated particles having an average diameter ranging from about two tenths of one millimeter to about five millimeters.

EXAMPLE V

Thirty grams of polymer particles of Example I were placed in a stainless steel mixing bowl. Seventy grams of an ester including 0.1 percent of pigment were used as an active ingredient and blended into the particles in the mixing bowl until the ester and the pigment had been uniformly dispersed and entrapped in the particles. Three liters of water was placed in a six liter vessel and heated to eighty degrees Centigrade. One hundred grams of stearoxy dimethicone silicone wax was added to the heated water and agitated until uniformly dispersed. With continued agitation, the polymer particles containing the entrapped pigment were added to the vortex of the six liter vessel and the agitation was continued for about one minute. Heating was discontinued and two liters of water at thirty-two degrees Centigrade was added to the six liter vessel under agitation. Agitation was discontinued and coacervated particles floated to the surface. The water was decanted and the coacervated particles were collected, spread evenly in trays, and dried at about thirty degrees Centigrade.

EXAMPLE VI

Example V was repeated, except that 23.2 grams of the powder particles of Example I were employed, and 29.6 grams of polydimethylcyclosiloxane fluid was used as the active ingredient. A coacervating agent mixture was prepared containing 15.0 grams of ceresin wax having a melting point of 68–72 degrees Centigrade and 27.0 grams of stearoxy dimethicone silicone wax. The wax mixture also contained 5.2 grams of D&C Green No. 6 dye as a color additive. The resulting coacervated particles were found suitable for incorporation into hair shampoo formulations.

The present invention should be distinguished from the concept taught in U.S. Pat. No. 3,989,649, issued Nov. 2, 1976, which relates to a polymer particle of porous structure formed by the use of wax as a pore former. In the '649 patent, the wax pore former is removed from the polymer particle by solvent extraction resulting in a porous polymer particle which is otherwise free of active ingredient. In contrast and in accordance with the present invention, not only is the porous polymer particle loaded with an active ingredient which is not extracted, but the loaded particles including an active ingredient are in turn coacervated together with other loaded particles by a wax coacervating agent which constitutes a part of the final composition.

While the foregoing disclosure specifies various uses of the materials of the present invention, as well as various types and compositions of ingredients which may be entrapped within these and similar materials, the patent literature is replete with uses and ingredients which may be entrapped in such materials. For example, U.S. Pat. No. 4,690,825, discloses as active ingredients lubricants, emollients, moisturizers, pigments, insect or flea repellents, fragrances, vitamins, and drugs. When the active ingredient is a drug, it is said to include anti-infectives such as antibiotics, fungicides, scabicides, pediculicides, iodine, anti-inflammatory agents, antipruritics, astringents, anti-hidrotics, keratolytic agents, caustics, keratoplastic agents, rubefacients, sunscreens, demukents, protectants, and detergents. Uses of loaded beads includes cosmetic preparations such as hand creams, acne products, deodorants, antiperspirants, baby powders, foot powders, body powders, lip ices, lip sticks, baby creams and lotions, mouthwashes, dentifrices, medicated facial creams and lotions, shampoos, shaving creams, pre- and after-shave lotions, depilatories, and hairgrooming preparations.

U.S. Pat. No. 4,724,240, names as active ingredients ethylhexyl oxystearate, arachidyl propionate, ethylhexyl adipate, isopropyl myristate, ethanol, stearyl alcohol, propylene glycol, propionic acid, stearic acid, polyoxypropylene cetyl alcohol, carbowax, polyethylene glycol, petroleum jelly, mineral oil, mineral spirits, lanolin, acetylated lanolin, isopropyl lanolate, hexamethyldisiloxane, cyclic polydimethylsiloxanes, polyphenylmethylsiloxanes, polydimethyl-trimethylsiloxanes; phenyl, ethyl, and vinyl-substituted polysilanes; and cosmetic dyes. Materials loaded with such ingredients are said to be useful in cosmetic, beauty, toiletry, and healthcare products, insecticides, disinfectants, flavors, perfumes, antiperspirant wax or oil base sticks, deodorants, colognes, pressed powders, and toilet soaps.

Entrapped functional materials in the Published European Application No. 0252463A2 are said to encompass pigments, perfumes, pheromones, synthetic insect attractants, pesticides including juvenile hormone analogs, herbicides, pharmaceuticals, antimicrobial agents, sunscreens, light stabilizers, fragrances, flavors including sweeteners, and various chemicals. Of the various chemicals disclosed are menthol, soybean oil, Vitamin E, salicylic acid, squalane, simethicon, bromochlorinated paraffin, benzophenone, petroleum distillate, jojoba oil, and citrus oil. The published application also specifically identifies and names four pheromones, twenty pesticides, twenty-three fragrances, about thirty-seven chemicals, and some twenty-two emollients, that may be entrapped in the materials as active ingredients.

In the Patent Cooperation Treaty International Publication No. WO/88/01164, there is also listed as specifically named ingredients which may be loaded into the beads approximately twenty-two ultraviolet absorbers, nineteen insect repellants, and thirty emollients. The publication also names several steroids including adrenocortical steroids such as fluocinolone, fluocinolone acetonide, triamcinolone acetonide, beta-methasone valerate, timobesone acetate, hydrocortisone, hydrocortisone acetate, triamcinolone, prednisolone, prednisolone acetate, dexamethasone, beclomethasone dipropionate, betamethasone diproprionate, betamethasone benzoate, clocorolone pivalate, halcinonide, flumethasone pivalate, and desonide.

European Published Application No. 0306236A2, published Mar. 3, 1989, discloses "in situ" and "post absorbed" suspension polymerized beads loaded with six different categories of active ingredients. The six categories of active ingredients are hair growth promoters, acne treatments, fragrances, vitamins, pain relievers, and epidermal lipid substitutes. The hair growth promoter is Minoxidil. For acne treatment there is employed benzoyl peroxide, salicylic acid, and resorcinol. Fragrances include flower oils, essential oils, animal and synthetic fragrances, and resinoids. Some thirty-nine specific fragrances are named. Vitamins include A, D, E, K, B1, B2, B12, B15, B17, C, niacin, folic acid, panthotenic acid, biotin, bioflavinoids, choline, inositol, and F. Cod liver oil and retinoids are also disclosed. Some twenty-two pain relievers, and some twenty-two mixtures and combinations of various pain relievers are disclosed, among which are menthol, camphor, and methyl salicylate. The epidermal lipid substitutes are squalane and squalene. The six categories of loaded beads may be used alone or as topical applications in creams, ointments, lotions, and oils. In addition, the fragrance loaded beads can be added to perfumes, colognes, cosmetics, soaps, paper products, detergents, and body and foot powders. The vitamin loaded beads also find application in lip balms, lipsticks, eye shadows, foundations, and blushers.

In U.S. Pat. No. 4,719,040, issued Jan. 12, 1988, a porous polymer powder laden with perfume is included as an ingredient in an aqueous air freshener gel. U.S. Pat. No. 4,764,362, issued Aug. 16, 1988, and U.S. Pat. No. 4,813,976, issued Mar. 21, 1989, relate to emery boards including an emollient entrapped onto an absorbent acrylates copolymer powder. Filing of a nail releases the emollient which conditions and lubricates the nails and cuticles. A toothpaste containing dental flossing tape is disclosed in U.S. Pat. No. 4,776,358, issued Oct. 11, 1988. Included as an ingredient of the dentifrice are "microsponges" containing a flavor oil. In U.S. Pat. No. 4,828,542, issued May 9, 1989, copolymer bead and powder particles entrapping various functional materials are bonded to the surfaces of a reticulated polyurethane foam. Among the enumerated functional materials which may be entrapped are adhesives; pharmaceuticals such as insulin, interferon, albumin, hormones, and monoclonal antibodies; flavors; fragrances for perfume samplers, air fresheners, and drawer liners; colors; inks; liquid crystals; oils; waxes; solvents; resins; fire extinguishing agents; insect repellants for mothballs, and flea and tick applications; agricultural chemicals such as insecticides, fungicides, and pheromones; disinfectants; cosmetics such as skin lotions, hair care products, sunscreens, and mouth wash; vitamins; antiperspirants; contraceptives; medicants such as Benzocaine, transdermal drugs, analgesics, allergy bacteria, methyl salicylate, and nitroglycerin. Molded and layered articles are also disclosed.

It will be apparent from the foregoing that many other variations and modifications may be made in the structures, compounds, compositions, and methods described herein without departing substantially from the essential features and concepts of the present invention. Accordingly, it should be clearly understood that the forms of the invention described herein are exemplary only and are not intended as limitations of the scope of the present invention.

That which is claimed is:

1. A composition comprising discrete particles of a highly cross-linked macroporous polymer, the particles being of a first predetermined average diameter, the polymer particles having entrapped therein and dispersed uniformly throughout an active ingredient, the particles including unit particles of less than about one micron in average diameter, agglomerates of fused unit particles of sizes in the range of about twenty to eighty microns in average diameter, and aggregates of clusters of fused agglomerates of sizes in the range of about two-hundred to about twelve-hundred microns in average diameter, and a coacervating agent mixed with the polymer particles in an amount sufficient to cause the polymer particles to collect forming dense clusters of coacervated particles of a second predetermined average diameter, the second predetermined average diameter being substantially in excess of the first predetermined average diameter.

2. The composition of claim 1 wherein the polymer is hydrophobic and is formed of at least one polyunsaturated monomer.

3. The composition of claim 2 wherein the polyunsaturated monomer is selected from the group consisting of ethylene glycol dimethacrylate and tetraethylene glycol dimethacrylate.

4. The composition of claim 1 wherein the polymer is hydrophobic and is formed of at least one monounsaturated monomer and at least one polyunsaturated monomer.

5. The composition of claim 4 wherein the monounsaturated monomer is selected from the group consisting of lauryl methacrylate and 2-ethylhexyl methacrylate, and the polyunsaturated monomer is selected from the group consisting of ethylene glycol dimethacrylate and tetraethylene glycol dimethacrylate.

6. The composition of claim 1 in which the polymer particles constitute from about ten to about fifty percent by weight of the composition, the active ingredient from about five to about eighty percent by weight of the composition, and the coacervating agent from about ten to about seventy percent by weight of the composition.

7. The composition of claim 1 in which the second predetermined average diameter of the coacervated particles is from about two tenths of one millimeter to about five millimeters.

8. The composition of claim 7 in which the second predetermined average diameter of the coacervated particles is from about four tenths of one millimeter to about two millimeters.

9. The composition of claim 1 in which the polymer is a polymethacrylate.

10. The composition of claim 1 in which the coacervating agent is a wax selected from the group consisting of insect and animal waxes, vegetable waxes, mineral waxes, petroleum waxes, synthetic waxes, and silicone waxes.

11. The composition of claim 10 in which the wax is a mixture of a mineral wax and a silicone wax.

12. The composition of claim 11 in which the mineral wax is ceresin wax and the silicone wax is stearoxy dimethicone.

13. The composition of claim 10 including a dye.

* * * * *